US006578405B2

(12) United States Patent
Kleinberg et al.

(10) Patent No.: US 6,578,405 B2
(45) Date of Patent: Jun. 17, 2003

(54) GAS SEEP DETECTION

(75) Inventors: Robert L. Kleinberg, Ridgefield, CT (US); Neil W. Bostrom, Danbury, CT (US); Douglas D. Griffin, Bethel, CT (US); Peter G. Brewer, Carmel, CA (US)

(73) Assignee: Schlumberger Technology Corporation, Ridgefield, CO (US)

( * ) Notice: Subject to any disclaimer, the term of this patent is extended or adjusted under 35 U.S.C. 154(b) by 0 days.

(21) Appl. No.: 09/962,063

(22) Filed: Sep. 25, 2001

(65) Prior Publication Data

US 2003/0056568 A1 Mar. 27, 2003

(51) Int. Cl.$^7$ ................................................. G01N 7/00
(52) U.S. Cl. ..................... 73/19.01; 73/23.2; 73/170; 181/120; 181/115; 367/141; 416/93 R
(58) Field of Search ................ 73/19.01, 23.2, 73/170.32; 181/120, 115; 416/93 R; 367/141

(56) References Cited

U.S. PATENT DOCUMENTS

| | | | |
|---|---|---|---|
| 2,918,579 A | * 12/1959 | Slobod et al. | ............... 250/255 |
| 3,571,591 A | * 3/1971 | Bradley et al. | ............. 250/255 |
| 3,961,187 A | * 6/1976 | Barringer | .................... 250/253 |
| 4,092,858 A | * 6/1978 | Edgerton | ................. 73/170.29 |
| 6,128,949 A | 10/2000 | Kleinberg | ................. 73/152.18 |

OTHER PUBLICATIONS

V.T. Jones et al., "Gas chromatographic and sonar imaging of hydrocarbon seeps in the marine environment", 1988, Remote Sensing for Geology, vol. 1, pp. 125–134.*

A. W. Adamson. "The Formation of a New Phase—Nucleation and Crystal Growth". Physical Chemistry of Surfaces, Third Edition, (1976), Chapter VIII, pp. 372–384.

A. L. Anderson et al. "Acoustics of Gas–Bearing Sediments I. Background". Journal of the Acoustical Society of America 67, (1980), pp. 1865–1889.

A. L. Anderson et al. "Acoustics of Gas–Bearing Sediments II. Measurements and Models". Journal of the Acoustical Society of America 67, (1980), pp. 1890–1903.

W. S. Burdic. Underwater Acoustic System Analysis, Second Edition (1991) pp. 86–88.

T. G. Leighton. The Acoustic Bubble. Academic Press (1994), Chapter 4.4.7, pp. 413–424.

* cited by examiner

Primary Examiner—Daniel S. Larkin
Assistant Examiner—André K. Jackson
(74) Attorney, Agent, or Firm—Jody Lynn DeStefanis; William B. Batzer; John J. Ryberg

(57) ABSTRACT

A method of detecting a marine gas seep that includes: deploying a local probe on or near the seafloor; producing bubbles in water near or within the local probe; detecting the bubbles; producing data indicating the relative concentration of dissolved gas in the water; and associating elevated dissolved gas concentrations with the presence of a nearby marine gas seep. Another aspect of the invention involves an apparatus configured to carry out the inventive method. Preferred embodiments of the invention utilize an ultrasonic transducer to both produce bubbles and detect them.

22 Claims, 7 Drawing Sheets

GAS SEEP DETECTION

FIELD OF THE INVENTION

This invention relates to the detection of geologic features and, more particularly, to the detection of marine gas seeps.

BACKGROUND

Natural gas seeps are widespread underneath the world's oceans and seas. Gas, predominantly methane, is generated by the bacterial decomposition of organic matter in shallow sediments. Thermal cracking of hydrocarbons at greater depths also generates gas. Where the seafloor depth is greater than about 500 meters below sea level, and where temperatures are sufficiently low, this gas will combine with water to form gas hydrate. Gas hydrate is a form of ice in which a considerable amount of natural gas is trapped in the crystallographic cages formed by solid water. Hydrate is typically found in a band a few hundred meters thick below the seafloor.

The petroleum industry is very interested in detecting the presence of gas hydrate. There are formidable technical problems connected with drilling wells on the continental shelf and continental slope in the presence of hydrates. Solid hydrate frequently acts to cement sediments in which it exists, and this semi-consolidated mass may overlay highly fluidized unconsolidated sediment residing below the lower boundary of the hydrate stability zone. This is very similar to the conditions that cause avalanches on snow-covered slopes. In fact there is evidence of massive subsea slumps in areas known to have significant accumulations of hydrates. Such slumps can be significant hazards to oil and gas exploration and production operations.

Gas hydrates may also become a significant source of fossil fuel in the future. Enormous quantities of natural gas are trapped in hydrate reservoirs just beneath the seafloor. Many of these deposits are found in the exclusive economic zones of the United States, Canada, Japan, and Russia, relatively near energy consumers. While seismic prospecting has located many such deposits, it has been found that this method has missed some sizable accumulations.

Geochemical exploration surveys have been used to map the presence and distribution of oil and gas seepage and to help identify areas with a high potential for petroleum reservoirs. Exploration Technologies, Inc. of Houston, Tex., for instance, advertises that they have developed a wide range of marine geochemical sampling tools, including sediment coring, geochemical drilling, bottom water sampling, surface slick sampling, and a Sniffer system. The Sniffer system reportedly pumps a continuous stream of sea water from a height of approximately 10 meters above the seabed to one or more gas chromatographs located aboard a ship that continuously analyzes "stripped gases for methane through butane light hydrocarbons". Disadvantages of the Sniffer system apparently include the following: it is limited to water depths of about 600 feet or less; it may be difficult to deploy on seismic vessels with limited space; it is generally limited to light hydrocarbon analysis; it may not give reliable results in areas with very low seepage rates; and it has limited availability. Any analysis method that transports samples from near the seafloor to the water's surface introduces potential sample handling problems and increases the delay time between sample collection and analysis. An improved method and apparatus for locating marine gas seeps is clearly desirable.

It is not uncommon for deep-sea equipment to observe bubbles of methane rising from the seafloor. It has also been observed that where no rising bubbles are apparent, disturbing the sediment will sometimes release gas. In still other instances, a sample of seawater will outgas when transported upwards in the water column. These observations indicate that methane is at or near its bubble point in seawater at many locations.

Even if methane is dissolved in water at its saturation concentration, bubble production may not occur. The gas phase can be thermodynamically stable at a given temperature and pressure, but a gas bubble cannot form because its surface free energy exceeds the free energy difference of the bulk phases. This phenomenon accounts for supercooling, superheating, or supersaturation commonly observed at first order phase transitions, and is described by classical nucleation theory. See, for instance, A. W. Adamson, "Physical Chemistry of Surfaces", 3rd edition, Wiley, 1976, chap. 8.

Other types of gases may be released by marine gas seeps, including carbon dioxide, nitrogen, and hydrogen sulfide. One potential application for an improved marine gas seep detection system is to monitor subsea reservoirs in which carbon dioxide is being sequestered or natural gas is being stored.

For these reasons, it would be of great benefit to be able to identify gas seeps with a local probe that can be deployed on or near the seafloor.

SUMMARY OF INVENTION

One aspect of the invention involves a method of detecting a marine gas seep that includes: deploying a local probe on or near the seafloor; producing bubbles in water near or within the local probe; detecting the bubbles; producing data indicating the relative concentration of dissolved gas in the water; and associating elevated dissolved gas concentrations with the presence of a nearby marine gas seep. Another aspect of the invention involves an apparatus configured to carry out the inventive method. Preferred embodiments of the invention utilize an ultrasonic transducer to both produce bubbles and detect them. Further details and features of the invention will become more readily apparent from the detailed description that follows.

BRIEF DESCRIPTION OF FIGURES

The invention will be described in more detail below in conjunction with the following Figures, in which.

DETAILED DESCRIPTION

Figure 1:
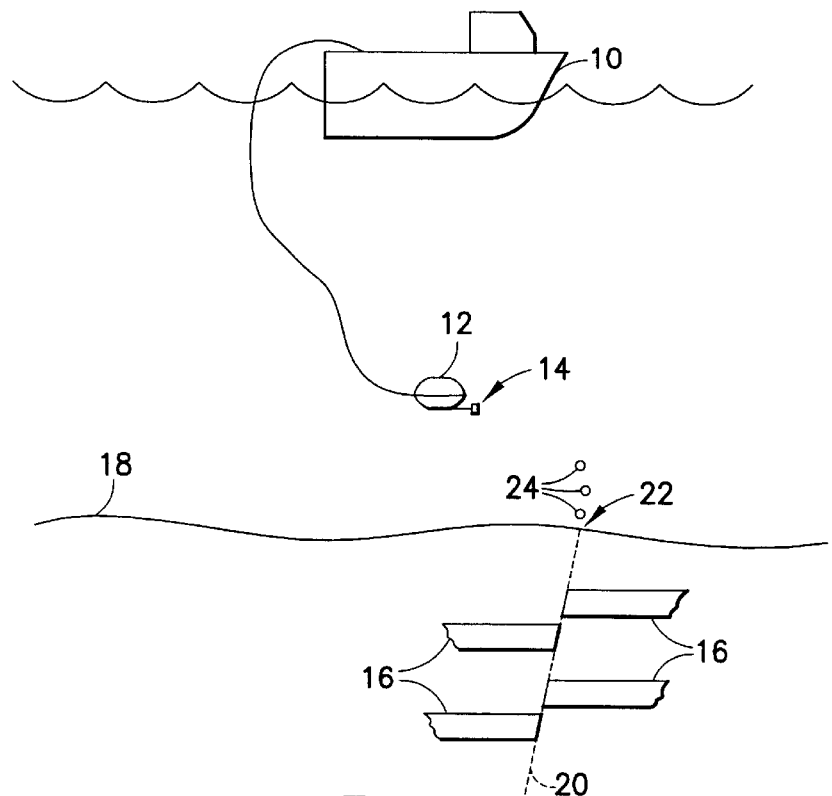
FIG. 1 schematically represents the detection of a marine gas seep in accordance with certain embodiments of the invention.

FIG. 1 shows equipment associated with the detection of a marine gas seep in accordance with certain embodiments of the invention. In FIG. 1, a ship 10 is used to control a remote operated vehicle 12 onto which a local probe 14 has been mounted. Natural gas from source rocks at depth has formed a series of gas hydrate deposits 16 beneath the seafloor 18. A portion of the gas forming the gas hydrate deposits 16 also migrates upwardly toward the seafloor 18 along geologic fault or fracture 20. The area in which the gas escapes the sediment and enters the water column is referred to as gas seep 22. In FIG. 1, the quantity of gas escaping from the subsurface is so large that bubbles 24 are being formed in the seawater above gas seep 22.

Figure 2:
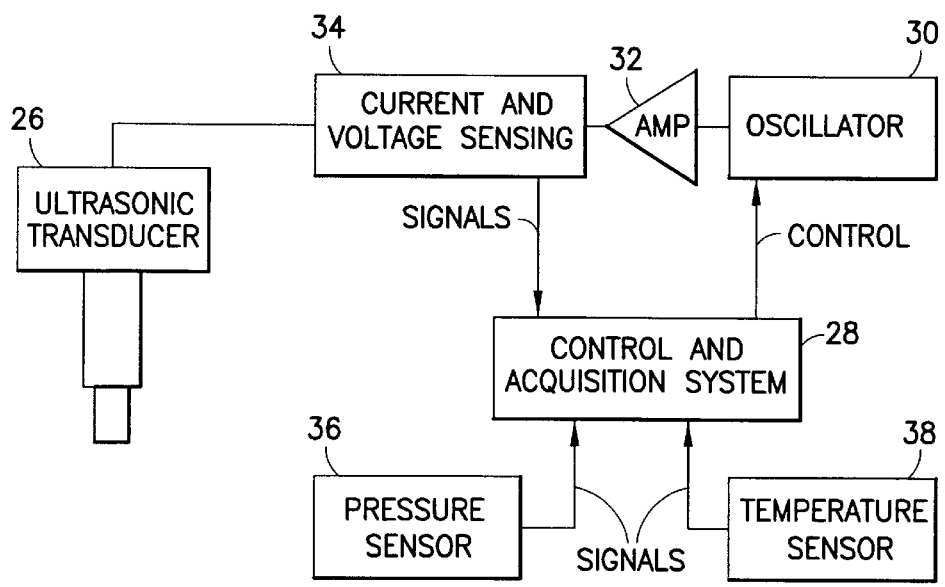
FIG. 2 schematically illustrates components associated with operating a local probe in accordance with certain embodiments of the invention.

The local probe may be deployed on a remotely operated vehicle, as shown in FIG. 2, to survey a preselected area of interest at the ocean floor. Alternately, an autonomous underwater vehicle can survey a wider area of interest, and report its findings after return to the surface or recovery. The local probe may also be permanently installed at the seafloor or on an underwater structure associated with oil or gas exploration, drilling, or production activities. The local probe may be used, for instance, to monitor local dissolved gas concentrations during exploration or production drilling operations to help avoid potential problems associated with drilling in areas where hydrates are known or suspected or to monitor the integrity of marine reservoirs being used for carbon dioxide sequestration or natural gas storage.

The inventive method of detecting a marine gas seep involves deploying the local probe 14 on or near the seafloor 18; producing bubbles in water near or within the probe; detecting these bubbles; producing data indicating the relative concentration of dissolved gas in the water; and associating locally elevated dissolved gas concentrations with the presence of a nearby marine gas seep 22. Data indicating the relative concentration of dissolved gas in the water (which may be binary data, i.e. "high concentrations of dissolved gas detected" vs. "high concentrations of dissolved gas not detected") may be used, for instance, to produce maps of the seafloor indicating local dissolved gas concentrations and the locations of suspected marine gas seeps.

For surveys in deep water and in subsea sediments, a piston-type ultrasonic transducer that can simultaneously produce and detect the bubbles is most convenient. One example of this type of transducer is a high power ultrasonic homogenizer. The radiation and sensitivity pattern of this type of transducer is focussed in one direction. This type of transducer can, for example, be pushed down into sediments to detect methane below the seafloor surface.

FIG. 2 illustrates electrical components associated with certain embodiments of the local probe circuitry. A feedback system is used to maintain the transducer at its resonance frequency, and to ensure that its power output is constant. The time constant of the control loop (approximately 1 sec) is long compared to the characteristic time of bubble-related fluctuations (around 0.001 sec). FIG. 2 illustrates, in block diagram form, a system for generating electrical drive, detecting a cavitation signal and stabilizing the power output of the ultrasonic transducer. A benefit of this type of system is its ability to both generate and detect cavitation with one transducer.

An oscillator 30 operates at a variable frequency set by the control system 28. An acoustic frequency around 20 kHz has been found to be convenient. The oscillator 30 feeds an amplifier 32 to provide energy to drive the transducer. The drive signal to the transducer 26 can be a monochromatic cw waveform of constant magnitude. In the presence of cavitation, bubbles form and collapse thereby changing the radiation efficiency and modulating the amplifier output voltage and current.

For most efficient operation, the natural frequency of vibration of the transducer 26 and the frequency of the transmitter electronics should coincide. The transducer operating frequency and electrical properties change with environmental and loading conditions. Therefore, current and voltage sensing circuits 34 monitor the feed line of the transducer 26. The current and voltage signals are fed to a data acquisition digitizer 28 for processing. The control system 28 analyzes the phase of the signals and generates a feedback signal to drive the transducer 26 at its resonant frequency. This maximizes the system's energy efficiency. Current and voltage are also used in feedback to maintain constant power to the transducer 26.

Digital processing can be used to extract the components of in-phase and out-of-phase current and voltage. These are used to compute the operating frequency and transmitted power of the transducer 26. Alternatively, the current and voltage signals can be processed with analog circuitry, for example with lock-in amplifiers. Both digital and analog control methods have been used successfully. The feedback system for the transducer operation can have a frequency response of 1 Hz.

When no gas bubbles are present near the transducer 26, its radiation efficiency is relatively constant. Bubbles are detected by monitoring fluctuations of the transducer current and voltage. It has been found that acoustic signals associated with bubble motion occur in at least the 100 Hz to 3000 Hz frequency range.

The amplifier output voltage squared is one simple and useful parameter to demodulate and measure. The cavitation-induced modulation can be detected digitally by the acquisition system 28 or with an appropriate analog demodulator. The feedback system is purposely too slow to null electrical variations in the kilohertz frequency range. In a properly designed system, the statistical variance of electrical measurements can increase by three orders of magnitude or more in the presence of bubbles.

If needed to limit heating in the vicinity of the transducer, pulse mode operation can be used. The selection of pulse width and duty cycle is a compromise between heating and the quantity of data that can be accumulated per unit time. High power sound pulses are for example 0.1 seconds long. At many times during this interval, one or more indicators of radiation efficiency are instantaneously detected and recorded. The statistical properties of each of these indicators are then computed digitally over the duration of one or more pulses. Low power is optionally applied to the transducer between high power pulses.

If desired, the pressure (or depth) of the local probe as well as the temperature may be measured and sent to the Control and Acquisition System 28 by a Pressure Sensor 36 and Temperature Sensor 38, respectively. Temperature measurements may be particularly helpful because marine gas seeps are often associated with local changes in seafloor temperatures.

The blocks in the diagram shown in FIG. 2 suggest a certain division of functions but it will be known to those practiced in electronics that these functions can be readily combined or divided in other ways.

The theoretical background underlying the embodiment of this local probe design will now be elaborated and experimental confirmation of the theoretical background will be presented.

Background Theory

An ultrasonic transducer can create gas bubbles by cavitation. Cavitation has generally been considered to be impossible when the fluid pressure is high—above a few hundred atmospheres. Since pressure at the seafloor may be 100 atm or higher, it would appear that cavitation would be excluded. However, for a fluid at or near the bubble point, modest localized pressure reductions, such as those that are caused by acoustic waves, can lead to efficient evolution of bubbles. See for instance, commonly-assigned U.S. Pat. No. 6,128,949 to R. L. Kleinberg, entitled "Phase Change Analysis in Logging Method", incorporated herein by reference.

Various other means may be used to induce cavitation, such as propellers. However, the ultrasonic method is particularly suitable for sensing methane within sediments beneath the seafloor, where a propeller or other moving body will not typically operate.

It is as important to sense the presence of bubbles as it is to generate them. Ideally, bubbles should be sensed at the site at which they are produced, i.e. at the ultrasonic transducer used for cavitation. Several methods can be used. The radiation efficiency of an ultrasonic transducer is extremely sensitive to the presence of bubbles. Hence, bubbles can be produced and sensed at the same site, with very high reliability. Changes in radiation efficiency are reflected in changes in the electrical measurements made on the transducer.

The transmission of sound from one medium (e.g. the solid surface of a transducer) to a second medium (e.g. the fluid under test) is controlled in part by the acoustic impedance of the fluid. The acoustic impedance Z of a medium is defined by the product of its density, $\rho$, and the speed of sound in it, v. Thus $Z=\rho v$. It is well known how to design ultrasonic transducers that radiate efficiently into a single-phase liquid medium such as seawater.

The presence of bubbles changes both the speed of sound and the density of the liquid. Thus there is a sudden change in the radiation efficiency of the transducer when bubbles are produced. Moreover the radiation pattern of a transducer is the same as its sensitivity pattern, a result of the reciprocity principle. Hence, the location at which bubbles are most readily produced—the site of highest acoustic amplitude—is the same location to which the transducer is most sensitive to changes in the acoustic properties of the fluid. Thus bubbles are produced and sensed at the same site, with very high reliability.

The radiation efficiency can be monitored by measuring the electrical properties of the transducer while it is being driven. We have found that the most appropriate choice of electrical parameter to sense depends on the design of the driver circuit, among other things. Changes in resonance frequency, voltage, voltage squared, current, current squared, phase angle between current and voltage, power dissipation, electrical impedance, combinations of these, or other electrical indications can all be useful indicators of bubble presence. In one exemplary implementation, the voltage across the transducer is monitored and applied to a squaring circuit. A demodulator and digitizer are used to record $V^2$ as a function of time during the high power pulse.

In another implementation, the electrical parameter $V \cdot I \cdot \sin\phi$ was monitored during the pulse, where $\phi$ is the phase angle between the voltage V and current I. Note that no time-delayed acoustic waveform is detected.

This technique has been applied to a mixture of methane and n-heptane in a model flow line apparatus surrounded by a coaxial-cylinder type ultrasonic resonator. The experimental results are shown in Voltage-Squared Waveform Display 40 shown in FIG. 3. The time record of $V^2$ in the single-phase region is the flat line 42 shown in FIG. 3. After the pressure was lowered and bubbles produced, the voltage increased, as shown by the noisy line 44. The increase was due to a change in the transducer's acoustic radiation efficiency. Put another way, when no bubbles are present near the transducer, the squared and demodulated voltage across the ultrasonic transducer is quiet during a high power pulse (flat line 42). In the presence of bubbles, $V^2$ is both higher and erratic (noisy line 44).

Various environmental conditions, such as temperature and pressure changes, can also cause the transducer acoustic and electrical properties to vary. An unambiguous indicator of bubble presence is the fluctuation of an electrical property. In the absence of bubbles, the acoustic and electrical properties of the transducer vary slowly, if at all. On the other hand, when bubbles are formed by cavitation, they can rapidly collapse, vibrate, or move. Any of these bubble motions affects the sound field of the transducer. We have found that even tiny and/or transient bubbles give rise to large fluctuations of resonance frequency, voltage, voltage squared, current, current squared, phase angle between current and voltage, power dissipation, electrical impedance, combinations of these, and other electrical indications.

Figure 3:
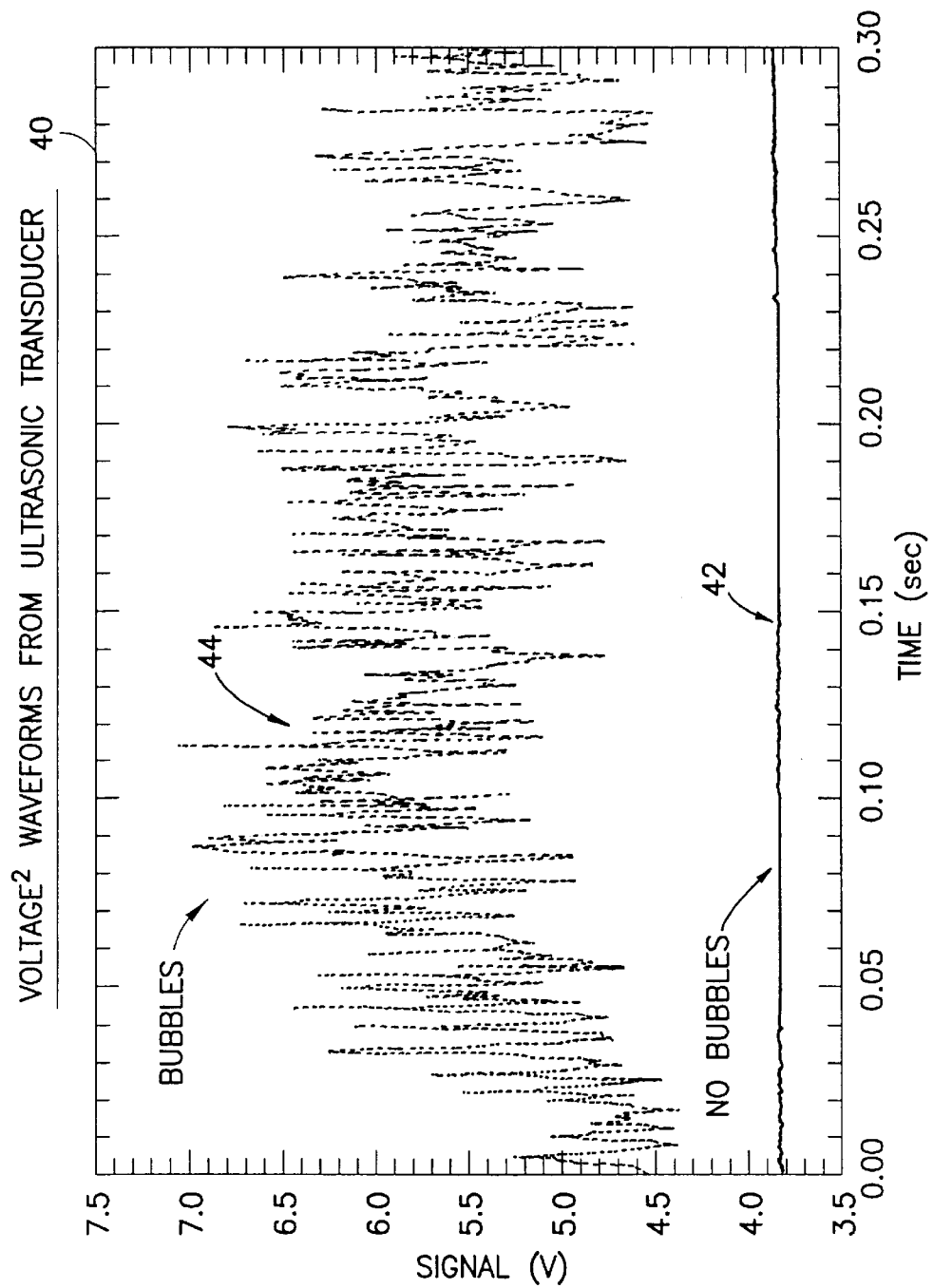
FIG. 3 illustrates squared and demodulated voltages across an ultrasonic transducer in the presence and absence of bubbles near the transducer.
Figure 4:
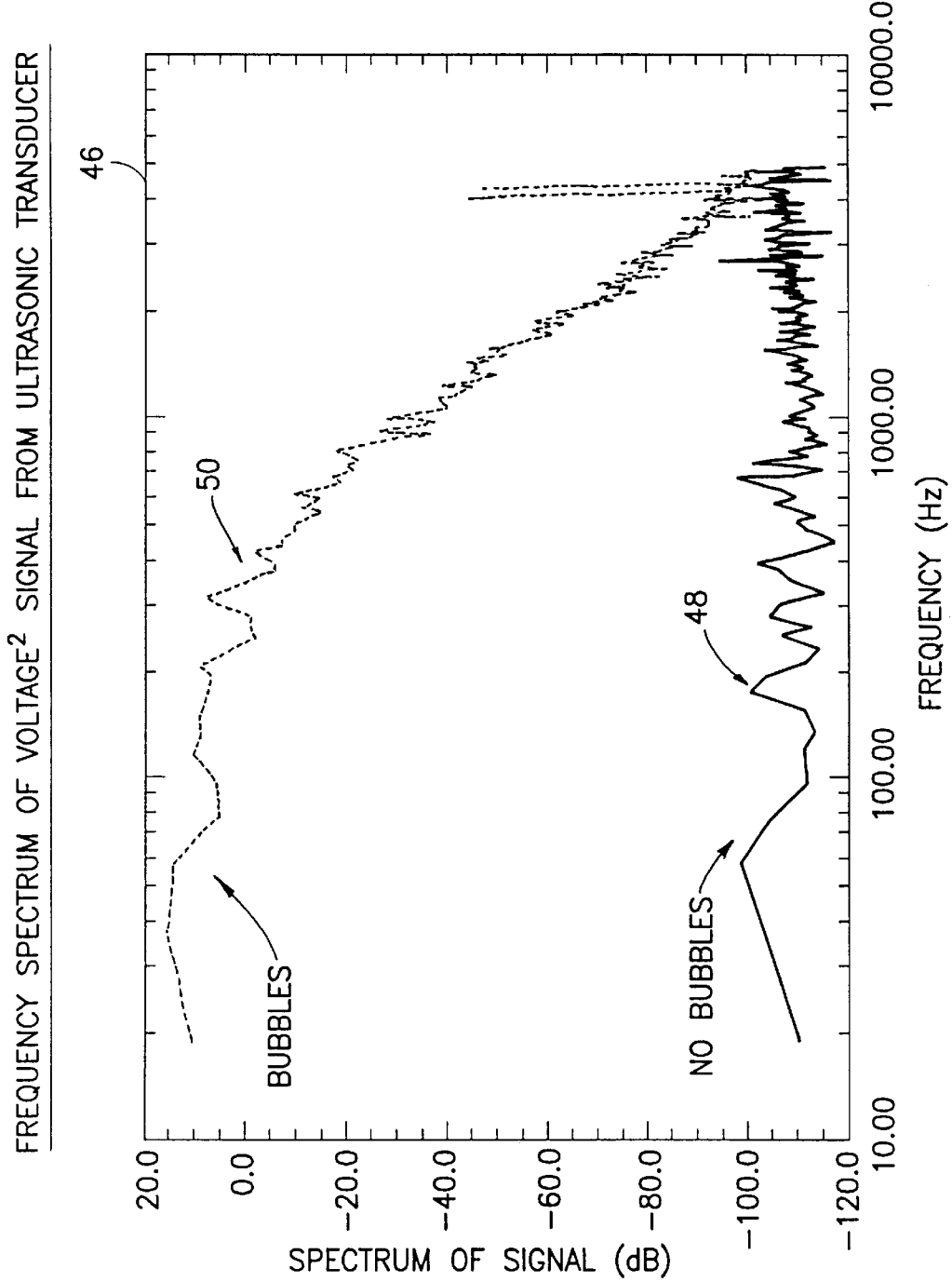
FIG. 4 illustrates the frequency spectrum of the time records shown in FIG. 3.

The frequency spectrum of the fluctuations gives insight into the processes by which bubbles affect the electrical properties of an acoustic transducer. The Fourier transforms of the time records of FIG. 3 are shown in FIG. 4 as Frequency Spectrum Display 46. In the absence of bubbles, the frequency spectrum is flat and reflects the noise floor of the measurement (no-bubble line 48 in FIG. 4). In the presence of bubbles, the spectrum has high power at low frequency, and drops rapidly above about 500 Hz as a result of bubble dynamics (bubble line 50 in FIG. 4). This suggests that fluctuating bubble processes are occurring on a time scale of milliseconds.

Experimental Confirmation of Background Theory

The dissolved gas detector was tested at room temperature and realistic pressures using a piston-type ultrasonic transducer in a high-pressure cell. A television camera imaged the interior of the cell, allowing independent confirmation of the presence of gas bubbles.

Solutions were prepared by dissolving nitrogen gas in water at high pressure. Nitrogen is a good analogue of methane in water solution. The transducer was activated at its resonant frequency and a preset peak power, and the pressure of the water solution was slowly reduced until cavitation occurred.

Figure 5:
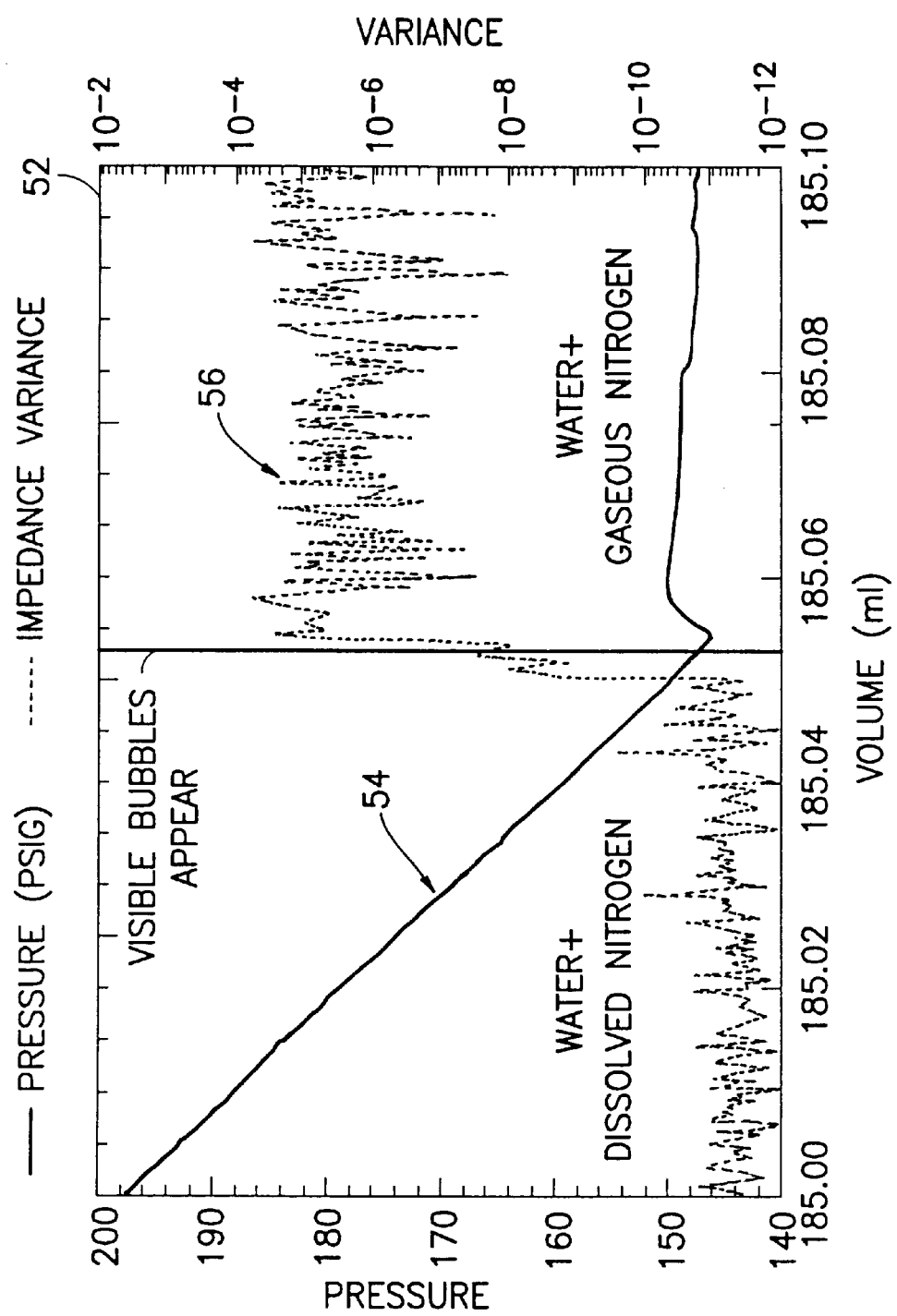
FIG. 5 illustrates the results of a first test verifying the ability of an ultrasonic transducer to produce and detect bubbles at elevated pressure.

Typical laboratory results that verify the ability of an ultrasonic tranducer to produce and detect nitrogen bubbles at elevated pressure are shown in FIG. 5 as First Experiment Display 52. When the fluid pressure is reduced to the nitrogen saturation pressure, the slope of pressure vs. volume curve 54 (i.e. compressibility) changes, the amplitude of the variance of the transducer electrical impedance curve 56 jumps by several orders of magnitude, and visible bubbles appear. The bubble point of the fluid was detected in these three ways: (1) by the visible appearance of bubbles in the video images, (2) by a sharp change of compressibility, and (3) by an electrical indication of the presence of bubbles. All three methods were coincident indicators of bubble formation in the test apparatus.

In field use, the detector may be moved from place to place, thereby sampling regions having differing degrees of gas saturation. In many situations, e.g. probing sediments below the seafloor, it may be inconvenient or inpossible to measure compressibility or use a video camera to detect the presence of bubbles. Electrical indications of bubble formation are typically better for detecting the presence of bubbles in these difficult conditions.

Acoustic methods can be used to estimate the bubble point even when the ambient pressure is somewhat above the bubble point pressure. When the sound pressure level is increased, the peak-to-peak variation of pressure is increased. When the pressure in the rarefaction half-cycle dips below the bubble pressure, transient cavitation can occur. The rarefaction pressure is related to the transducer power by $$W = \frac{p^2 AF}{2\rho c E}$$

where
- W=electrical power supplied to transducer (watt)
- p=sound pressure (N/m$^2$)
- A=area of transducer face (piston model) (m$^2$)
- p=fluid density (kg/m$^3$) (water=1000)
- c=fluid speed of sound (m/s) (water=1500)
- E=transducer efficiency
- F=frequency factor The frequency factor accounts for the reduced cavitation efficiency at high frequency, see Burdic, Underwater Acoustic System Analysis, 1991. Below 10 kHz, it is approximately unity.

Figure 6:
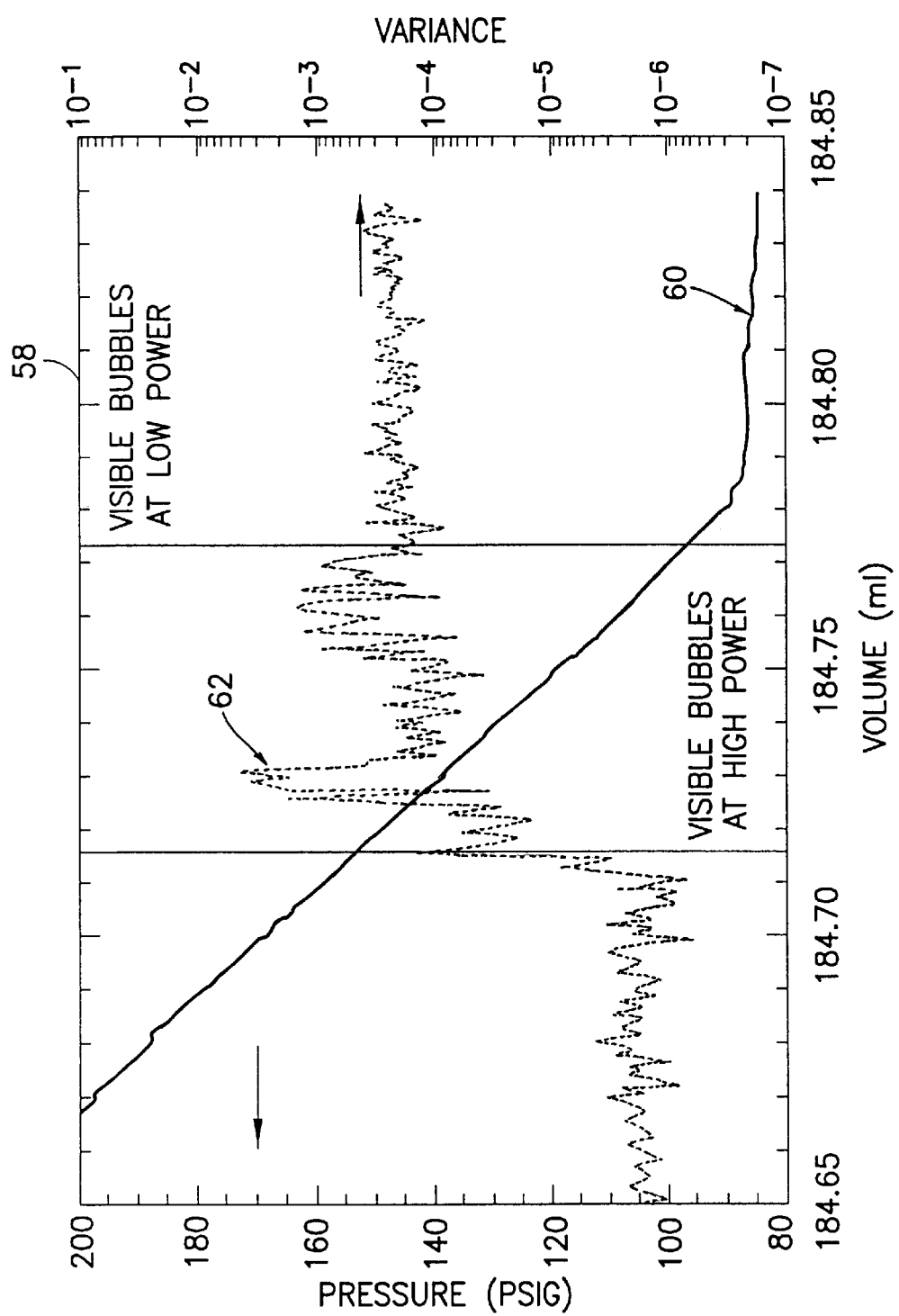
FIG. 6 illustrates the results of a second test verifying the ability of an ultrasonic transducer to produce and detect bubbles at elevated pressure, even when the ambient pressure is somewhat above the bubble pressure.

FIG. 6 presents results that show that bubble formation can be induced by cavitation even when the ambient pressure is well above the bubble pressure. Nitrogen dissolved in water was irradiated by 30 W pulses of 53 kHz acoustic energy from a piston transducer. Between the 30 W pulses, 0.5 W of continuous wave energy was applied. The piston transducer had a diameter of 1 cm, an efficiency of 0.9, and a frequency factor of about 10. Bubble creation was monitored by video camera and by measuring the variance of an electrical characteristic of the transducer while the power was being applied. In Second Experiment Display 58, the pressure vs. volume curve 60 and the variance of the transducer's electrical impedance curve 62 are overlaid, as in FIG. 5.

With 30 watts applied, bubbles were detected both visually and electrically at approximately 150 psig, about 65 psi above the bubble point for this solution. The variance measure increased by several orders of magnitude. The video observations suggested that the bubbles were transient, appearing only when high power was radiated by the transducer. With 0.5 watts applied, bubbles were detected visually and electrically about 10 psi above the bubble point.

Figure 7:
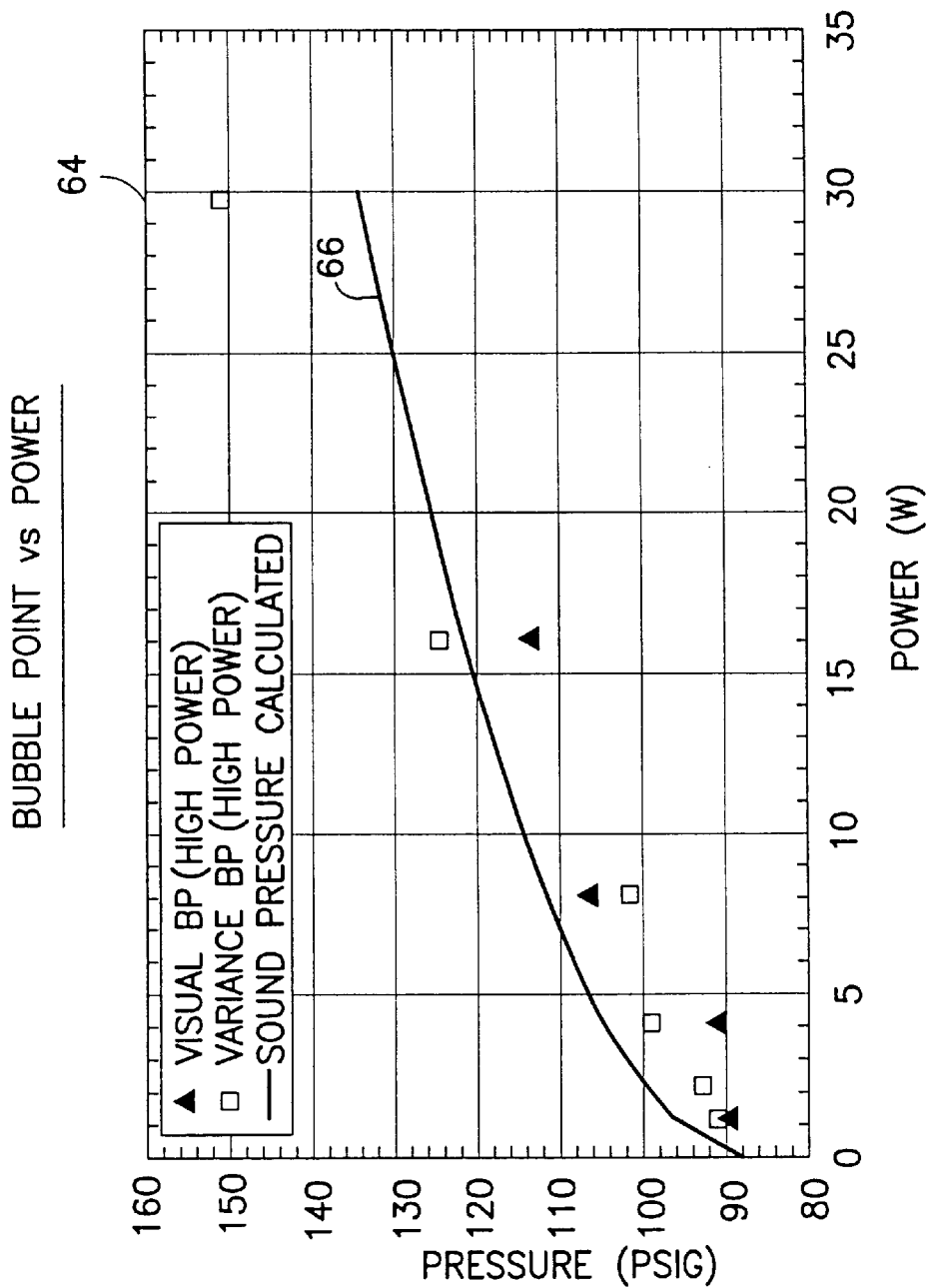
FIG. 7 illustrates the results of a series of measurements that confirm that the first appearance of bubbles approximately follows the expected power dependence relationship.

A series of experiments have shown that the pressure of first appearance of bubbles approximately follows the expected power dependence. The Bubble Point vs. Power Display 64 shown in FIG. 7 demonstrates that the bubble point pressure determined by both visual detection of bubbles (filled triangles) and by increased variance in transducer electrical properties (open squares) generally follows the calculated total pressure line 66 (the sum of the bubble point pressure (88 psi) and the calculated sound pressure level). As power increases, bubbles are seen (visually and electrically) at higher ambient pressures. Agreement with the theory (with no adjustable parameters) is fair. Thus, the true bubble pressure, here 88 psig, can be estimated from a single measurement at elevated power, together with knowledge of the transducer characteristics.

Alternative Methods and Apparatus

Numerous alternative embodiments of the inventive method and apparatus are possible. In one alternative implementation, methane-laden seawater is directed through a tube to an acoustic transducer of any design, including, for example, a coaxial cylindrical transducer. The tube may, for instance, be part of a coiled tubing system. Visual or optical systems for detecting bubble formation may be used.

Other physical phenomena may be used to detect the presence of bubbles. The presence of gas bubbles in a liquid has a large effect on both the speed and attenuation of sound. See, for instance, A. L. Anderson and L. D. Hampton, "Acoustics of Gas-Bearing Sediments I. Background", Journal of the Acoustical Society of America 67:1865–1889 (1980); A. L. Anderson and L. D. Hampton, "Acoustics of Gas-Bearing Sediments II. Measurements and Models", Journal of the Acoustical Society of America 67:1890–1903 (1980). Thus if the acoustic radiation of the transducer is sensed by a second transducer acting as a receiver, the transit time will increase and the received amplitude will decrease in the presence of bubbles.

An even more sensitive indicator of the presence of bubbles is the generation of harmonics and subharmonics. Liquids and solids are linear elastic media. When sound is transmitted through them, speed, wavelength and amplitude may be altered, but the frequency of the wave is not. However, bubbles are nonlinear elements. When they are excited by an acoustic wave at a particular frequency, their motions can generate acoustic waves at other frequencies. This is discussed in more detail in T. G. Leighton, The Acoustic Bubble, San Diego: Academic Press, 1994, Chap. 4.4.7. Thus the appearance of harmonics is an unmistakable indicator of bubbles.

Figure 8:
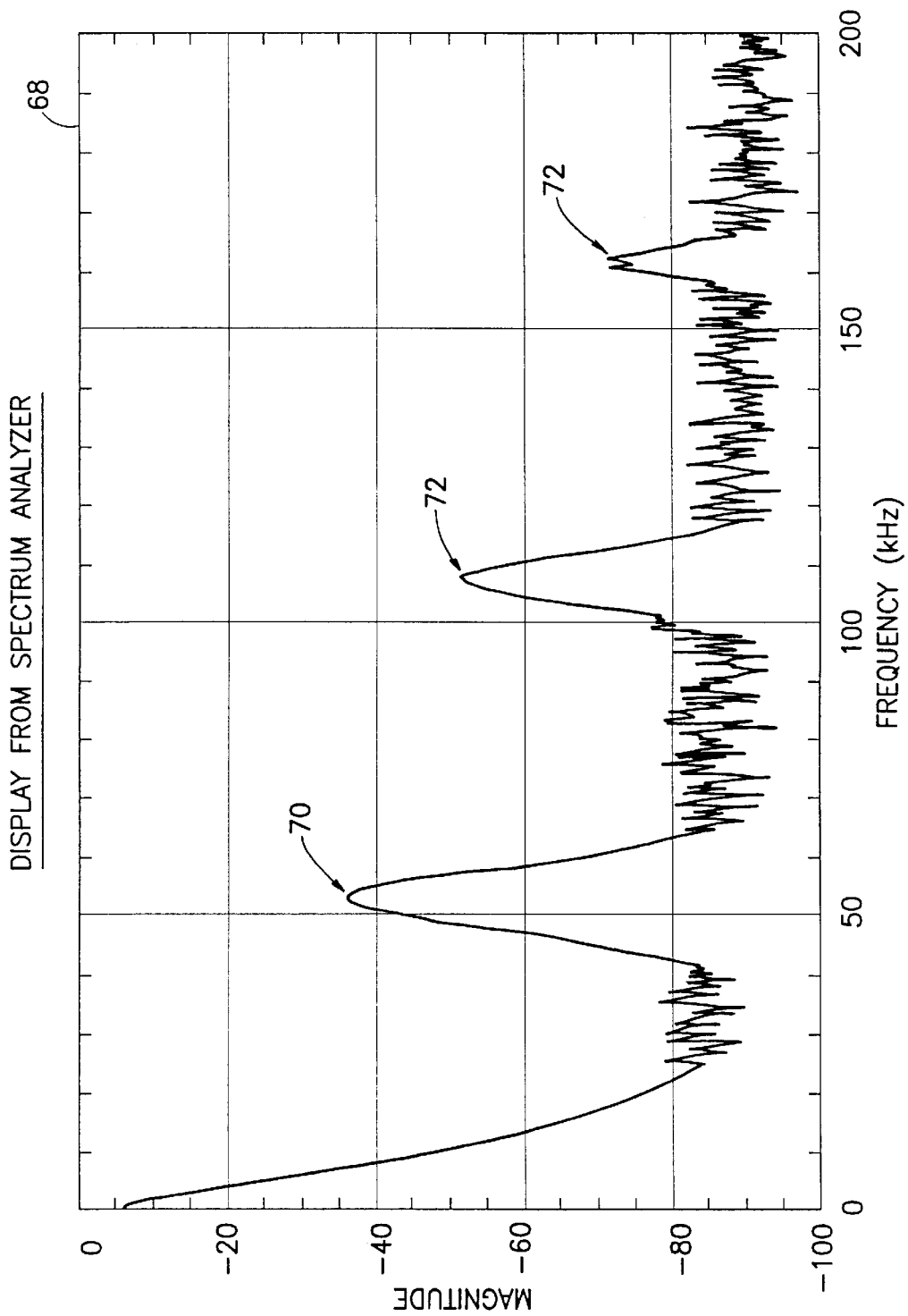
FIG. 8 illustrates the spectrum of a continuous wave signal of a receiver clamped to the outside of a pressure vessel in accordance with an alternative embodiment of the invention.

A cell was constructed in which sound was generated with a 1 cm diameter piston transducer, operating continuously at a frequency of 53 kHz. The transducer was in contact with the fluid, and used to generate gas bubbles near the bubble point. A broadband receiver was secured to the outside of the cell with a clamp; grease ensured good acoustic coupling. A video camera inside the cell was used to visually monitor bubble production. At pressures above the bubble point, the receiver detected sound only at 53 kHz (not shown). When bubbles were present, many Overtones 72 were observed in the spectrum of the continuous wave signal at the receiver in addition to the Primary 53 kHz Signal 70, as shown in the Spectrum Analyzer Display 68 depicted in FIG. 8.

While the invention has been described herein with reference to certain examples and embodiments, it will be evident that various modifications and changes may be made to the embodiments described above without departing from the scope and spirit of the invention as set forth in the claims.

We claim:

1. A method of detecting a marine gas seep, comprising:
   deploying a local probe on or near the seafloor;
   producing bubbles in water using said local probe;

detecting said bubbles; and producing data indicating the relative concentration of dissolved gas in said water.

2. A method according to claim 1, wherein said local probe utilizes an acoustic transducer to produce said bubbles.

3. A method according to claim 2, further including varying the energization of said local probe to start or terminate bubble production.

4. A method according to claim 3, wherein the energization level of said local probe at which bubble production starts or terminates is used to calculate the relative concentration of dissolved gas in said water.

5. A method according to claim 1, wherein said local probe is deployed by embedding said local probe in seafloor sediments.

6. A method according to claim 1, wherein said local probe utilizes an acoustic transducer to detect said bubbles.

7. A method according to claim 6, wherein changes in electrical response characteristics of said acoustic transducer are used to detect said bubbles and said changes in electrical response characteristics comprise changes to one or more of resonance frequency, voltage, voltage squared, current, current squared, phase angle between current and voltage, power dissipation, and electrical impedance.

8. A method according to claim 6, wherein said bubble production is detected by observing the presence of harmonics using said acoustic transducer.

9. A method according to claim 1, wherein said bubble production is detected by observing changes in electrical response characteristics of a transducer located within said local probe.

10. A method according to claim 1, wherein said bubble production is detected by visually or optically detecting the appearance of bubbles.

11. A method according to claim 1, further including measuring the pressure at which said bubbles are produced and detected.

12. A method according to claim 1, further including measuring the temperature at which said bubbles are produced and detected.

13. A method according to claim 1, wherein said local probe is deployed on a remote operated vehicle (ROV) or an autonomous underwater vehicle (AUV).

14. An apparatus for detecting a marine gas seep, comprising:

a local probe having means for producing bubbles in water adjacent to or within said local probe;

means for detecting said bubbles;

means for deploying said local probe on or near the seafloor; and means for producing data indicating the relative concentration of dissolved gas in said water.

15. An apparatus for detecting a marine gas seep, comprising:

a transducer;

control and acquisition circuitry, coupled to said transducer, for actuating said transducer and detecting bubbles produced by said transducer; and means for deploying said transducer on or near the seafloor.

16. An apparatus according to claim 15, wherein said transducer is an ultrasonic transducer.

17. An apparatus according to claim 16, wherein said control and acquisition circuitry analyzes signal phase and generates a feedback signal to drive said ultrasonic transducer at its resonant frequency.

18. An apparatus according to claim 17, wherein said control and acquisition circuitry's feedback system control loop has a time constant of approximately 1 second.

19. An apparatus according to claim 15, further including a temperature sensor.

20. An apparatus according to claim 15, wherein said control and acquisition circuitry actuates said transducer in pulse mode.

21. A method according to claim 1, further comprising associating elevated dissolved gas concentrations with the presence of a nearby marine gas seep.

22. An apparatus according to claim 15, further comprising means for associating elevated dissolved gas concentrations with the presence of a nearby marine gas seep.

\* \* \* \* \*